United States Patent
Holmberg

(10) Patent No.: US 12,145,003 B2
(45) Date of Patent: Nov. 19, 2024

(54) PROVIDING A TREATMENT PLAN FOR RADIOTHERAPY WHEN THE DELIVERY IS INTERRUPTED

(71) Applicant: RaySearch Laboratories AB, Stockholm (SE)

(72) Inventor: Rickard Holmberg, Stockholm (SE)

(73) Assignee: RaySearch Laboratories AB, Stockholm (SE)

( * ) Notice: Subject to any disclaimer, the term of this patent is extended or adjusted under 35 U.S.C. 154(b) by 202 days.

(21) Appl. No.: 17/783,205

(22) PCT Filed: Nov. 30, 2020

(86) PCT No.: PCT/EP2020/083908
§ 371 (c)(1),
(2) Date: Jun. 7, 2022

(87) PCT Pub. No.: WO2021/115820
PCT Pub. Date: Jun. 17, 2021

(65) Prior Publication Data
US 2023/0019727 A1    Jan. 19, 2023

(30) Foreign Application Priority Data
Dec. 11, 2019   (EP) ................................ 19215187

(51) Int. Cl.
*A61N 5/10*    (2006.01)

(52) U.S. Cl.
CPC ......... *A61N 5/1038* (2013.01); *A61N 5/1037* (2013.01); *A61N 5/1071* (2013.01)

(58) Field of Classification Search
CPC .................. G01N 21/3586; G01N 2021/3595
See application file for complete search history.

(56) References Cited

U.S. PATENT DOCUMENTS

| | | |
|---|---|---|
| 5,549,632 A | 8/1996 | Lai |
| 5,993,438 A | 11/1999 | Juhasz et al. |
| 6,325,792 B1 | 12/2001 | Swinger et al. |
| 2008/0240351 A1 | 10/2008 | Bohsung |
| 2018/0160994 A1 | 6/2018 | Harrington et al. |
| 2019/0021684 A1 | 1/2019 | Ruebel et al. |

FOREIGN PATENT DOCUMENTS

| | | | | |
|---|---|---|---|---|
| EP | 3434328 A1 | | 1/2019 | |
| EP | 3750595 A1 | * | 12/2020 | ........... A61N 5/1031 |
| EP | 3838343 A1 | * | 6/2021 | ........... A61N 5/1031 |
| JP | 2010-148534 A | | 7/2010 | |
| JP | 5399698 B2 | * | 1/2014 | ............... A61N 5/10 |
| WO | WO-2018/222751 A1 | | 12/2018 | |

* cited by examiner

*Primary Examiner* — David P Porta
*Assistant Examiner* — Fani Polyzos Boosalis
(74) *Attorney, Agent, or Firm* — Faegre Drinker Biddle & Reath LLP

(57) ABSTRACT

It is provided a method for providing a treatment plan for radiotherapy when the delivery is interrupted, the method being performed by a treatment planning system. The method comprises the steps of: detecting that delivery of a first treatment plan has been interrupted; obtaining an indication of delivery of a partial dose, representing the part of the first treatment plan that was delivered prior to the interruption; generating a second treatment plan, wherein the partial dose delivery forms an input to the second treatment plan generation as a background dose; and optimizing the second treatment plan while considering a plurality of scenarios.

9 Claims, 2 Drawing Sheets

PROVIDING A TREATMENT PLAN FOR RADIOTHERAPY WHEN THE DELIVERY IS INTERRUPTED

CROSS REFERENCE TO RELATED APPLICATIONS

This application is a National Stage of International Application No. PCT/EP2020/083908, filed Nov. 30, 2020, and claims the benefit of European Patent Application Ser. No. 19/215,187.6, filed Dec. 11, 2019, the entire contents of each of which are incorporated herein by reference.

TECHNICAL FIELD

The present disclosure relates to the field of radiotherapy and in particular to providing a treatment plan for radiotherapy when the delivery is interrupted.

BACKGROUND

In radiation therapy, a target volume is irradiated by one or several therapeutic beams. Various types of therapeutic beams can be used, e.g. photon, electron and ion beams. The target volume can represent a cancer tumor. The therapeutic beam penetrates tissue and delivers an absorbed dose to kill the tumor cells.

In a radiation therapy session for a patient, the delivery of radiotherapy sometimes has to be interrupted. The interruption can occur e.g. due to the patient needing to go to the bathroom or for technical reasons. In the prior art, when delivery of radiotherapy is resumed, the system simply provides the remainder of the delivery.

However, when the delivery is resumed, the patient may have moved or internal organs may have shifted or deformed compared to before (e.g. due to an emptied bladder).

US 2018/160994 A1 discloses systems and methods for planning and executing automated multi-axis motion in treatment.

SUMMARY

One object is to improve delivery of radiotherapy when delivery has been interrupted.

According to a first aspect, it is provided a method for providing a treatment plan for radiotherapy when the delivery is interrupted, the method being performed by a treatment planning system. The method comprises the steps of: detecting that delivery of a first treatment plan has been interrupted; obtaining an indication of delivery of a partial dose, representing the part of the first treatment plan that was delivered prior to the interruption; generating a second treatment plan, wherein the partial dose delivery forms an input to the second treatment plan generation as a background dose; and optimizing the second treatment plan while considering a plurality of scenarios.

In the step of generating the second treatment plan, the first treatment plan is used in a dose reference objective function used in the generating of the second treatment plan.

The method may further comprise the step of: obtaining a future treatment plan; in which case, in the step of generating, a combination of the first treatment plan and the future treatment plan, is used in a dose reference objective function used in the generating of the second treatment plan.

The plurality of scenarios may comprise different patient translations.

The plurality of scenarios may comprise different breathing phase orientations.

The plurality of scenarios may comprise different organ orientations.

The background dose may represent a radiation dose external to the second treatment plan.

According to a second aspect, it is provided a treatment planning system for providing a treatment plan for radiotherapy when the delivery is interrupted, the treatment planning system comprising: a processor; and a memory storing instructions that, when executed by the processor, cause the treatment planning system to: detect that delivery of a first treatment plan has been interrupted; obtain an indication of delivery of a partial dose, representing the part of the first treatment plan that was delivered prior to the interruption; generate a second treatment plan, wherein the partial dose delivery forms an input to the second treatment plan generation as a background dose; and optimize the second treatment plan while considering a plurality of scenarios.

The instructions may comprise instructions that, when executed by the processor, cause the treatment planning system to use the first treatment plan in a dose reference objective function used in the generating of the second treatment plan.

The treatment planning system may further comprise instructions that, when executed by the processor, cause the treatment planning system to: obtain a future treatment plan; and use a combination of the first treatment plan and the future treatment plan in a dose reference objective function used in the generating of the second treatment plan.

The plurality of scenarios may comprise different patient translations.

The plurality of scenarios may comprise different breathing phase orientations.

The plurality of scenarios may comprise different organ orientations. Different organ orientation is here to be interpreted as different organ geometries (size, shape, position, etc.).

The background dose may represent a radiation dose external to the second treatment plan.

According to a third aspect, it is provided a computer program for providing a treatment plan for radiotherapy when the delivery is interrupted. The computer program comprises computer program code which, when run on a treatment planning system causes the treatment planning system to: detect that delivery of a first treatment plan has been interrupted; obtain an indication of delivery of a partial dose, representing the part of the first treatment plan that was delivered prior to the interruption; generate a second treatment plan, wherein the partial dose delivery forms an input to the second treatment plan generation as a background dose; and optimize the second treatment plan while considering a plurality of scenarios.

According to a fourth aspect, it is provided a computer program product comprising a computer program according to the third aspect and a computer readable means on which the computer program is stored.

Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise. The steps of any method disclosed herein do not have to be performed in the exact order disclosed, unless explicitly stated.

BRIEF DESCRIPTION OF THE DRAWINGS

Aspects and embodiments are now described, by way of example, with reference to the accompanying drawings, in which:

FIG. 5 shows one example of a computer program product comprising computer readable means.

DETAILED DESCRIPTION

The aspects of the present disclosure will now be described more fully hereinafter with reference to the accompanying drawings, in which certain embodiments of the invention are shown. These aspects may, however, be embodied in many different forms and should not be construed as limiting; rather, these embodiments are provided by way of example so that this disclosure will be thorough and complete, and to fully convey the scope of all aspects of invention to those skilled in the art. Like numbers refer to like elements throughout the description.

Figure 1A:
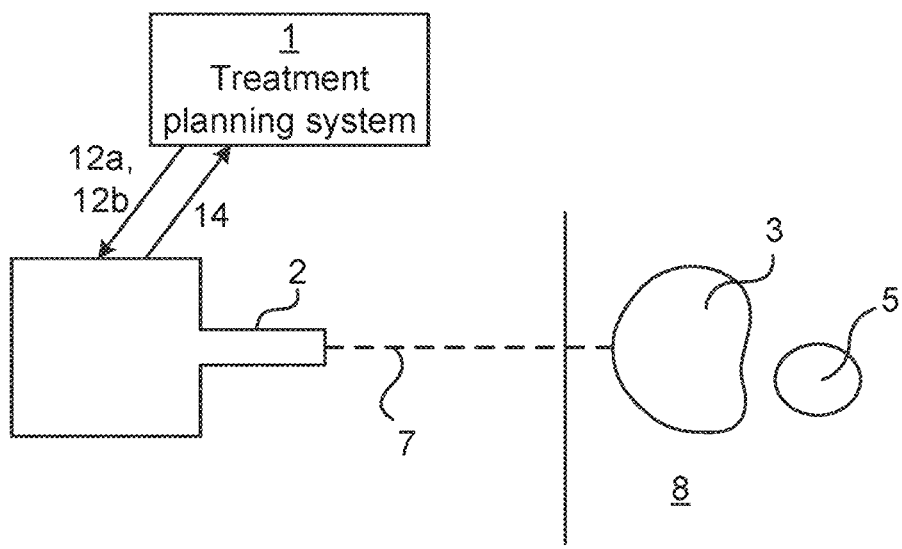
FIGS. 1A-1B are schematic drawings illustrating environments in which embodiments presented herein can be applied and FIG. 1B is a schematic diagram illustrating functional modules of the treatment planning system of FIG. 1A.
Figure 1B:
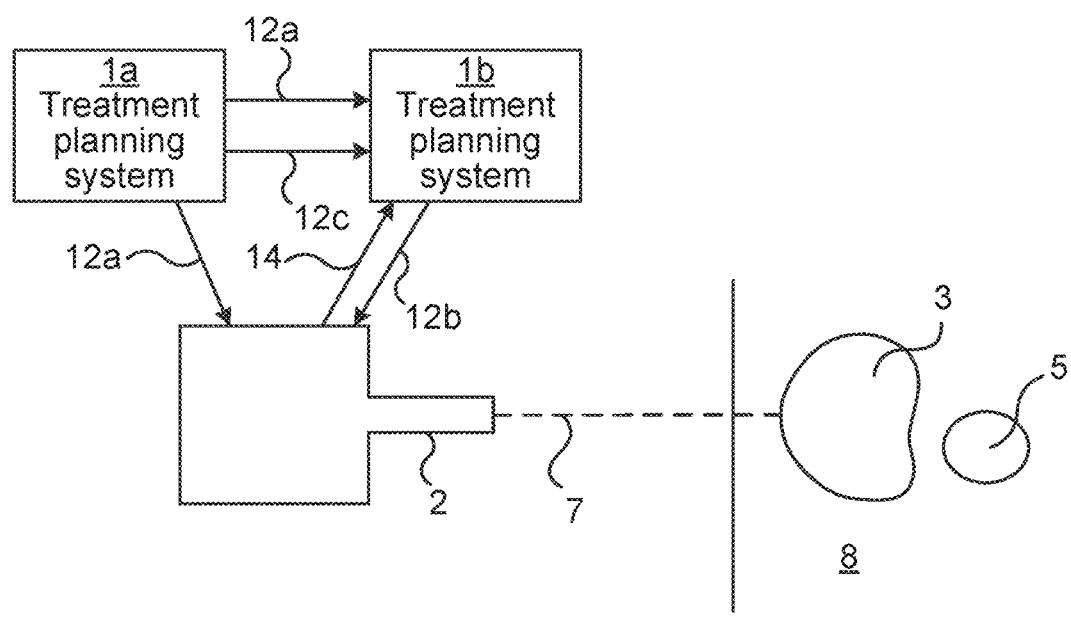

FIGS. 1A-B are schematic drawings illustrating environments in which embodiments presented herein can be applied. First, the embodiments of FIG. 1A will be described. A treatment planning system 1 determines a distribution radiation for radiation therapy. This is communicated as a treatment plan 12a, 12b to a radiation delivery system 2. Based on the treatment plan, the radiation delivery system 2 generates a beam 7 for providing radiation to a target volume 3 of a patient, while avoiding radiation to an organ at risk 5.

The way in which the radiation delivery system 2 generates the beam and delivers the dose differs depends on the treatment modality (such as photons, electrons, or ions) as is well known in the industry per se. However, the common goal is to deliver a dose to the target volume (i.e. the tumor) 3 that is as close as possible to a prescribed dose while minimizing the dose to organs at risk 5 such as bladder, brain and rectum depending on where the tumor is located.

According to embodiments presented herein, the treatment planning system is configured to manage delivery of radiotherapy when delivery is interrupted. This results in a sequence of treatment plans. Specifically, a first treatment plan 12a is provided to the radiation delivery system 2. The radiation delivery system 2 proceeds and starts generation of radiation delivery. However, the delivery is interrupted, after which an indication of delivery 14 is provided to the treatment planning system 1. The indication of delivery 14 can e.g. be in the form of logs indicating the radiation delivery to the patient in the delivery session prior to the interruption. The treatment planning system 1 then determines a second treatment plan 12b and provides this to the radiation delivery system 2.

Looking now to FIG. 1B, only differences compared to FIG. 1A will be described. In this embodiment, there is a first treatment planning system 1a and a second treatment planning system 1b. In this embodiment, the first treatment planning system 1a determines the first (original) treatment plan 12a. The second treatment planning system 1b determines the second treatment plan 12b. In order to determine the second treatment plan 12b, the first treatment planning system 12a provides the first treatment plan 12a and optionally future treatment plan(s) 12C. The second treatment planning system 1b also obtains the indication of delivery 14 from the radiation delivery system 2.

Figure 2:
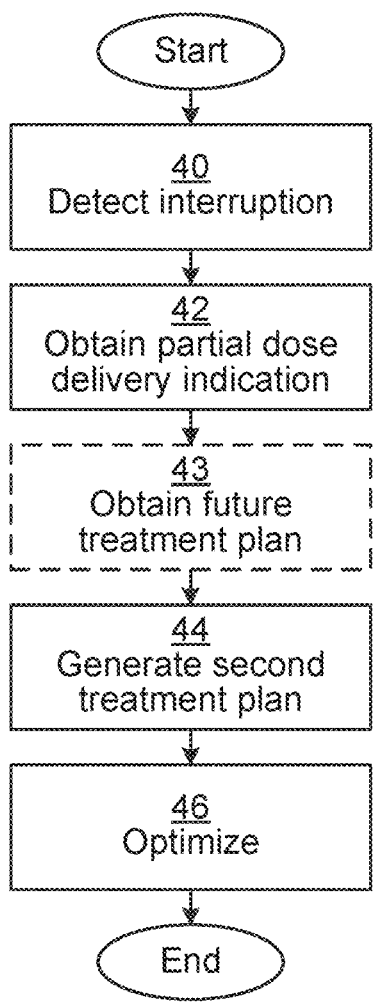
FIG. 2 is a flow chart illustrating methods for providing a treatment plan for radiotherapy when the delivery is interrupted.

FIG. 2 is a flow chart illustrating methods for providing a treatment plan for radiotherapy when the delivery is interrupted. The method being performed in the treatment planning system.

In a detect interruption step 40, the treatment planning system detects that delivery of a first treatment plan has been interrupted. This can be detected by information received from the radiation delivery system indicating that radiation delivery in accordance with the first treatment plan has been interrupted.

In an obtain partial dose delivery indication step 42, the treatment planning system obtains an indication of delivery of a partial dose, representing the part of the first treatment plan that was delivered prior to the interruption. This indication of delivery can e.g. be in the form of logs, from the radiation delivery system, indicating the radiation delivery to the patient in the delivery session prior to the interruption.

In an optional obtain future treatment plan step 43, the treatment planning system obtains a future treatment plan. The future treatment plan can e.g. be a treatment plan of a future session for the same patient. This can be obtained from the treatment planning system or other system storing the future treatment plan.

In a generate second treatment plan step 44, the treatment planning system generates a second treatment plan, wherein the partial dose delivery forms an input to the second treatment plan generation as a background dose. The background dose represents a radiation dose external to the second treatment plan.

Moreover, the first treatment plan can be used in a dose reference objective function used in the generating of the second treatment plan.

When step 43 is performed, a combination of the first treatment plan and the future treatment plan can be used in a dose reference objective function used in the generating of the second treatment plan. The combination may be calculated such that the combination provides the same biological effective dose as the first treatment plan and the future treatment plan. In other words, the remaining radiation delivery of the interrupted session is included in a future session.

In an optimize step 46, the treatment planning system optimizes the second treatment plan while considering a plurality of scenarios. The plurality of scenarios can comprise different patient translations, breathing phase orientations and/or different organ orientations. By considering the plurality of scenarios, a robust optimization is achieved in the way that small changes in these factors do not have major effects on the delivery of radiotherapy. The optimized plan can then be provided to the radiation delivery system.

When this method is not applied, the trivial solution of continuing with the remainder of the original treatment plan can result in dose overlap and/or dose gaps, e.g. due to patient translation (movement) or internal organ movement or deformation (e.g. an emptied bladder). Using embodiments presented herein, since a new optimization is performed to deliver the remaining radiation, a more robust plan is achieved, and the probability of significant dose overlap and/or dose gaps when delivering continuation sessions is dramatically reduced.

Figure 3:
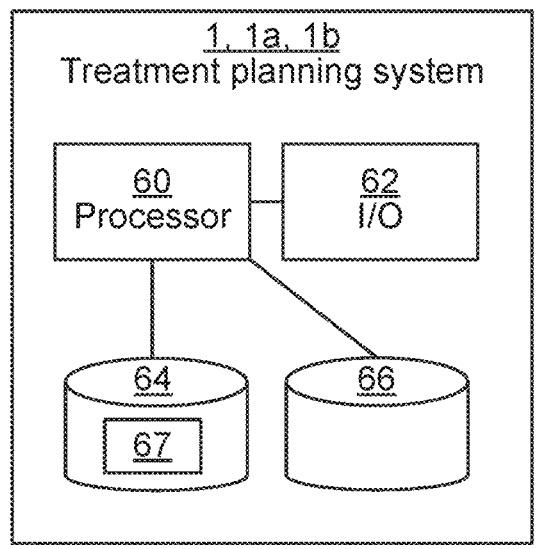
FIG. 3 is a flow chart illustrating embodiments of a method for generating a plurality of potential treatment plans, the method being performed in the treatment planning system of FIG. 1A.

FIG. 3 is a schematic diagram illustrating components of the treatment planning system 1, 1a-b of FIGS. 1A-B. A processor 60 is provided using any combination of one or more of a suitable central processing unit (CPU), multiprocessor, microcontroller, digital signal processor (DSP), etc., capable of executing software instructions 67 stored in a memory 64, which can thus be a computer program product. The processor 60 could alternatively be implemented using an application specific integrated circuit (ASIC), field programmable gate array (FPGA), etc. The processor 60 can be configured to execute the method described with reference to FIG. 2 above.

The memory 64 can be any combination of random-access memory (RAM) and/or read-only memory (ROM). The memory 64 also comprises persistent storage, which, for example, can be any single one or combination of magnetic memory, optical memory, solid-state memory or even remotely mounted memory.

A data memory 66 is also provided for reading and/or storing data during execution of software instructions in the processor 60. The data memory 66 can be any combination of RAM and/or ROM.

The treatment planning system 1 further comprises an I/O interface 62 for communicating with external and/or internal entities. Optionally, the I/O interface 62 also includes a user interface.

Other components of the treatment planning system 1 are omitted in order not to obscure the concepts presented herein.

Figure 4:
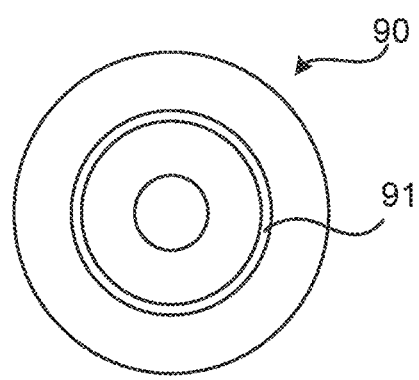
FIG. 4 is a schematic diagram illustrating components of the treatment planning system of FIG. 1A according to one embodiment.

FIG. 4 shows one example of a computer program product 90 comprising computer readable means. On this computer readable means, a computer program 91 can be stored, which computer program can cause a processor to execute a method according to embodiments described herein. In this example, the computer program product is an optical disc, such as a CD (compact disc) or a DVD (digital versatile disc) or a Blu-Ray disc. As explained above, the computer program product could also be embodied in a memory of a device, such as the computer program product 64 of FIG. 3. While the computer program 91 is here schematically shown as a track on the depicted optical disk, the computer program can be stored in any way which is suitable for the computer program product, such as a removable solid-state memory, e.g. a Universal Serial Bus (USB) drive.

The aspects of the present disclosure have mainly been described above with reference to a few embodiments. However, as is readily appreciated by a person skilled in the art, other embodiments than the ones disclosed above are equally possible within the scope of the invention, as defined by the appended patent claims. Thus, while various aspects and embodiments have been disclosed herein, other aspects and embodiments will be apparent to those skilled in the art.

The invention claimed is:

1. A method for providing a treatment plan for radiotherapy when the delivery is interrupted, the method being performed by a treatment planning system and comprising the steps of:
    detecting that delivery of a first treatment plan has been interrupted;
    obtaining an indication of delivery of a partial dose, representing the part of the first treatment plan that was delivered prior to the interruption;
    generating a second treatment plan, wherein the partial dose delivery forms an input to the second treatment plan generation as a background dose; and
    performing robust optimization of the second treatment plan while considering a plurality of scenarios, wherein the plurality of scenarios comprises one or more of different patient translations, different breathing phase orientations, and different organ orientations.

2. The method according to claim 1, wherein in the step of generating the second treatment plan, the first treatment plan is used in a dose reference objective function used in the generating of the second treatment plan.

3. The method according to claim 1, further comprising the step of:
    obtaining a future treatment plan;
    wherein in the step of generating, a combination of the first treatment plan and the future treatment plan is used in a dose reference objective function used in the generating of the second treatment plan.

4. The method according to claim 1, wherein the background dose represents a radiation dose external to the second treatment plan.

5. A treatment planning system for providing a treatment plan for radiotherapy when the delivery is interrupted, the treatment planning system comprising:
    a processor; and
    a memory storing instructions that, when executed by the processor, cause the treatment planning system to:
    detect that delivery of a first treatment plan has been interrupted;
    obtain an indication of delivery of a partial dose, representing the part of the first treatment plan that was delivered prior to the interruption;
    generate a second treatment plan, wherein the partial dose delivery forms an input to the second treatment plan generation as a background dose; and
    perform robust optimization of the second treatment plan while considering a plurality of scenarios, wherein the plurality of scenarios comprises one or more of different patient translations, different breathing phase orientations, and different organ orientations.

6. The treatment planning system according to claim 5, wherein the instructions comprise instructions that, when executed by the processor, cause the treatment planning system to use the first treatment plan in a dose reference objective function used in the generating of the second treatment plan.

7. The treatment planning system according to claim 5, further comprising instructions that, when executed by the processor, cause the treatment planning system to:
    obtain a future treatment plan; and
    use a combination of the first treatment plan and the future treatment plan in a dose reference objective function used in the generating of the second treatment plan.

8. The treatment planning system according to claim 5, wherein the background dose represents a radiation dose external to the second treatment plan.

9. A non-transitory computer readable means on which a computer program is stored, the computer program for providing a treatment plan for radiotherapy when the delivery is interrupted, the computer program comprising computer program code which, when run on a treatment planning system causes the treatment planning system to:
    detect that delivery of a first treatment plan has been interrupted;

obtain an indication of delivery of a partial dose, representing the part of the first treatment plan that was delivered prior to the interruption;

generate a second treatment plan, wherein the partial dose delivery forms an input to the second treatment plan generation as a background dose; and performing robust optimization of the second treatment plan while considering a plurality of scenarios, wherein the plurality of scenarios comprises one or more of different patient translations, different breathing phase orientations, and different organ orientations.

* * * * *